United States Patent [19]

Hirano et al.

[11] Patent Number: 5,470,966
[45] Date of Patent: Nov. 28, 1995

[54] NEURAL α-CATENIN

[75] Inventors: Shinji Hirano, Okazaki; Naomi Kimoto, Kyoto; Yutaka Shimoyama, Hiratsuka; Setsuo Hirohashi, Chiyoda; Masatoshi Takeichi, Kyoto, all of Japan

[73] Assignee: Takara Shuzo Co., Ltd., Kyoto, Japan

[21] Appl. No.: 94,889

[22] Filed: Jul. 22, 1993

[30] Foreign Application Priority Data

Dec. 25, 1992 [JP] Japan .................................. 4-358026

[51] Int. Cl.$^6$ ............................ C12N 15/09; C12N 15/12
[52] U.S. Cl. ..................... 536/23.5; 435/69.1; 435/320.1
[58] Field of Search ........................ 536/23.5; 435/69.1, 435/320.1; 530/350

[56] References Cited

PUBLICATIONS

Cell, vol. 70, pp. 293–301, Jul. 24, 1992, "Identification of a Neural α–Catenin as a Key Regulator of Cadherin Function and Multicellular Organization".

Herrenknecht et al. 1991. Proc. Natl. Acad. Sci. 88:9156–9160.

Nagafuchi et al. 1991. Cell 65:849–857.

*Primary Examiner*—Keith C. Furman
*Attorney, Agent, or Firm*—Wenderoth, Lind & Ponack

[57] ABSTRACT

To provide a new catenin concerning with the function of cell-cell adhesion, a gene encoding said catenin, and a use of said gene.

Isolated neural α-catenin. A gene encoding neural α-catenin. A method of producing neural α-catenin by the method of genetic engineering. A method of controlling the function of cell-cell adhesion by using said gene. Antibodies capable of recognizing neural α-catenin. Amino acid sequense of said neural α-catenin and nucleotide sequence of said gene are also determined.

6 Claims, 1 Drawing Sheet

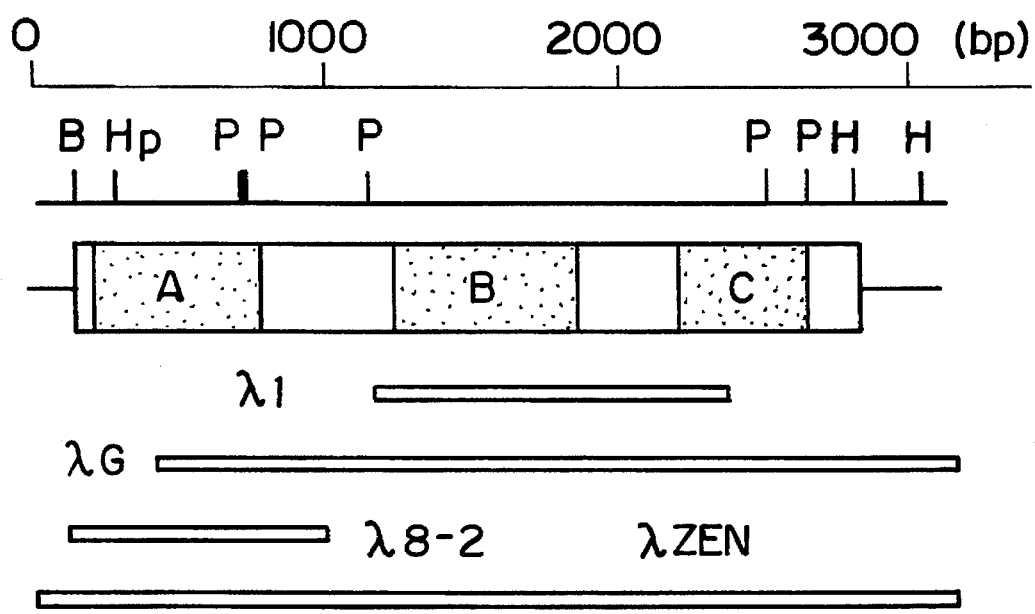

NEURAL α-CATENIN

FIELD OF THE INDUSTRIAL APPLICATION

This invention relates to neural α-catenin concerned with cell-cell adhesion, the gene encoding neural α-catenin, and the use of said gene.

PRIOR ART

Cadherins are transmembrane cell-cell adhesion receptors that are essential for vertebrate morphogenesis [*Science*, 251, p1451–1455 (1991)].

They colocalize with cortical actin bundles as well as other cytoskeletal proteins at cell-cell boundaries, and their actions are thought to be regulated by these cytoplasmic proteins [*The EMBO Journal*, 7, p3679–3684 (1988)]. Such proteins include catenins, which are directly associated with the cytoplasmic domain of cadherins [*Cell Regulation*, 1, p37–44 (1989)]. Cadherins whose catenin-binding sites were deleted cannot function as cell-cell adhesion molecules, although such deleted cadherins can be expressed on the cell surfaces. It is, therefore, believed that catenins might play some crucial roles in cadherin function.

Catenins have been classified into α, β, and γ on the basis of their electrophoretic mobilities [*The EMBO Journal*, 8, p1711–1717 (1989)]. α-Catenin was identified as a protein associated with E-cadherin [*Cell*, 65, p849–857 (1991)]. This protein, however, appears to be able to interact with other members of the cadherin family, such as N-cadherin and P-cadherin. In fact, this protein is expressed in a wide variety of embryonic tissues that express distinct cadherins. Among these tissues, however, embryonic brains exhibited a relatively low level of α-catenin expression [*Cell*, 65, p849–857 (1991)].

Problems to be solved by the Invention:

However, there has been no identification of protein mediating cadherin functions, except for α-catenin, in embryotic brain and nervous system, and their activity has not also been characterized yet.

The object of this invention is to provide a new catenin which is expressed a lot in nervous tissues including brain, a gene encoding said catenin, a method of producing said catenin, a method of using said gene, and antibodies capable of recognizing the said catenin.

Means for Solving the Problems:

To summarize, this invention relates to isolated neural α-catenin. This invention also relates to a gene encoding neural α-catenin. This invention also relates to a method of producing neural α-catenin. This invention also relates to a method of controlling the function of cell-cell adhesion. This invention also relates to an antibody which can recognize neural α-catenin.

The present inventors found that embryonic brains exhibit a relatively low level of α-catenin expression among a wide variety of embryonic tissues, and those findings led them to hypothesize that the brain might contain substitutes for α-catenin. Since one of the major cadherins expressed in the brain is N-cadherin, the inventors attempted to identify molecules associated with N-cadherin. In the next step, the inventors isolated the gene coding for this molecule and identified the nucleotide sequence.

Moreover, the inventors performed experiments in which an α-catenin-deficient cell line was transfected with said gene, expressed these molecules, and determined the function of the cell adhesive activities.

The inventors designated this molecule, which exists rich in nervous systems and mediates the function of N-cadherin, as neural α-catenin.

Moreover, the inventors determined the complete nucleotide sequence of the neural α-catenin cDNA and the deduced amino acid sequence of the cloned molecule. The inventors found that neural α-catenin shows similarity in part to α-catenin and vinculin. And then, the inventors identified that neural α-catenin was new α-catenin by immunological detection of this molecule in cell and tissues using anti-neural α-catenin antibodies, leading to the completion of this invention.

This invention is further explained in the following.

All animals who have nervous systems can be used in this invention. For example, chicken can be used. Any original material can be used here for nervous system. For example, embryonic brain is more suitable.

This invention is explained in details by using chicken embryonic brain for example as follows.

Isolation of N-cadherin-catenin complex can be performed, for example, by in vitro culturing tissues separated from a 10 day-old chick embryonic brain and immunopurifying antigens from their extracts using anti-N-cadherin monoclonal antibody immobilized on agarose gels.

Establishment of monoclonal antibodies against catenins by immunizing animals (including mice or rats) with N-cadherin-catenin complex, for example, is the initial step of isolation of catenins from N-cadherin-catenin complex. Next, catenins can be purified by immunoaffinity chromatgraphy using immobilized monoclonal antibodies directed to them. The inventors constructed two different monoclonal antibodies specific to said catenin and designated them as NCAT-1 and NCAT-2, respectively.

In order to characterize the molecular structure of the antigen recognized by these monoclonal antibodies, the cloned complementary DNA can be selected in a library from a chick embryonic brain and the amino acid sequences coding for the antigen can be deduced from the nucleotide sequence of the cloned gene. Nucleotide sequence of the obtained clone is shown by SEQ ID No. 2 in the sequence listing, and the amino acid sequence for the coding region is shown by SEQ ID No. 1 in the sequence listing. For example, this antigen can be determined to be a new subtype of α-catenin, by comparing the amino acid sequence with those of previously known α-catenin. The inventors designated this new subtype of α-catenin as neural α-catenin.

In order to determine that the protein for the above gene is reactive with this antibody, for example, the cadherin-positive cells endogeneously expressing no protein reactive with this antibody may be transfected with the above gene, and the expressed protein for the gene can be demonstrated to be reactive with this antibody.

Otherwise, for estimating the effect of neural α-catenin isolated as above on cadherin functions, for example, the cadherin- and β-catenin-positive cells, without surface expression of α-catenin, having no cell-cell contact may be transfected with the above gene and neural α-catenin can be produced by them. The control of cadherin function by neural α-catenin can be demonstrated to observe the construction of cell-cell contact by the expression of neural α-catenin. In addition, neural α-catenin can be realized to associate and interact with not only N-cadherin but also the other cadherins, for example, E-cadherin.

The study of tissue distribution for neural α-catenin can be performed as follows. For example, immunoblot analysis for several organs or tissues from a 4- to 10-day-old chick embryo using the above monoclonal antibody specific to neural α-catenin reveal that brain tissues contains higher amount of neural α-catenin, and that tissues highly expressing E-cadherin contain little neural α-catenin. In order to identify the coexistence of N-cadherin and neural α-catenin in neural tissues, immunohistochemical detection for the presence of N-cadherin and neural α-catenin in cell-cell contact sites of the cells isolated from chick embryonic brain, for example, glia cells, using anti-N-cadherin antibody or anti-neural α-catenin antibody can demonstrate the similar tissue distribution of N-cadherin and neural α-catenin,.

Neural α-catenin of this invention, for example, can be isolated from animal tissues including brain. In other ways, it can be produced by using the cells transfected with neural α-catenin gene in the manufacturing process. The measurement for neural α-catenin level in tissue, the observation or controlling of the expression for neural α-catenin in the progression, can be performed by using the gene which can hybridize with neural α-catenin gene obtained in this invention or the antibody against neural α-catenin. For further medical application, the substances showing the effect on the expression or function of neural α-catenin, for example, neural α-catenin protein, peptides for a part of the protein, antisense RNA against neural α-catenin gene, or antibodies specific to neural α-catenin, can be injected into the body as therapy for the diseases mediated by cell-cell adhesion process, for example, primary cancer, metastatic cancer, autoimmune disease, infection, dermal disease, or atherosclerosis.

BRIEF DESCRIPTION OF THE DRAWINGS

FIG. 1 shows the length of cDNA clones and the restriction map. A schematic diagram of molecular organization of the putative protein and the obtained four cDNA fragments (λ1, λG, λ8-2, λZEN) are also shown, in which A, B, and C are the regions similar to vinculino. Box indicates coding region. B, Hp, P, and H indicates BamHI, HpaI, PstI, and HindIII, respectively.

EXAMPLES

Below, this invention will be explained with reference to examples, but the invention is not to be taken to be limited to these examples. Example 1
1-1 Immunoaffinity Isolation of cadherin-catenin complex Whole brains isolated from 10-day-old chicken embryos were solubilized with extraction buffer (1% NP-40, 1% Triton X-100, and 1 mM $CaCl_2$ in 50 mM Tris-buffered saline (pH 7.6) (TBS) containing phenylmethylsulfonyl fluoride, pepstain, antipain, leupeptin, and p-toluenesulfonyl-L-arginine methyl ester hydrochloride) (2 ml per brain). After centrifugation, the supernatant was applied to a Sepharose CL-4B precolumn, then to NCD-2-conjugated immunoaffinity column [NCD-2 monoclonal antibody is described in *Nature*, 320, p474–449 (1986)], which was prepared by cross-linking purified NCD-2 antibodies to a protein A-conjugated Sepharose 4B using dimethyl pimelimidate dihydrochloride (Pierce). After thorough washing with TBS containing 1 mM $CaCl_2$, the antigen complexes were eluted with 50 mM triethylamine (pH 11.5) from the column. The eluted samples were immediately neutralized with 1M TBS (pH 8.0) and subjected to immunization of rats in order to generate monoclonal antibodies.
1-2 Generation of monoclonal antibodies NCAT-1 and NCAT-2

Donryu rats were immunized by several intraperitoneal injections of N-cadherin-catenin complexes obtained in example 1-1 emulsified with Freund's complete adjuvant; the materials obtained from about 25 brains were injected per animal. Three days after the last boost, cell fusion was performed using P3U1 myeloma and splenocytes of these animals, according to the method of Koehler and Milstein [*Nature*, 256, p495–497 (1975)]. Hybridomas were then screened for their ability to recognize catenin by immunoblotting, which is performed as follows: Samples were separated by SDS-polyacrylamide gel electrophoresis using 7.5% polyacrylamide gels. After electrophoresis, proteins were transferred to nitrocellulose. The sheets were incubated with 2.5% skim milk in TBS containing 1 ml $CaCl_2$. After incubation with first antibodies, signals were detected with iodinated second antibodies (Amersham) or using the biotinylated second antibodies and alkaline phosphatase-conjugated streptavidin system (Amersham). As a result, monoclonal antibodies NCAT-1 and NCAT-2 were obtained. NCAT-2 showed a higher affinity to the antigens than NCAT-1.
1-3 Immunoblotting analysis NCAT-1 and NCAT-2 monoclonal antibodies obtained in example 1-2 recognized the same antigens, each reacting with two proteins of 113 kd and 102 kd, in the immunoblots of whole brain lysates as well as of materials immunoprecipitated with N-cadherin. To examine whether N-cadherin is associated with any proteins, the inventors prepared monolayer cultures of 10-day-old chick embryonic brain cells, metabolically labeled with [$^{35}S$]methionine, and immunoprecipitated N-cadherin from the detergent extract of these cells. At least two proteins of 102 and 94 kd coprecipitated with N-cadherin, consistent with previous observations. The 113 kd component was not clearly detected in the autoradiograms of $^{35}S$-labeled N-cadherin immunoprecipitates; this is probably due to a lesser amount of this protein.

Example 2

2-1 cDNA cloning of NCAT-1 antigen
A λgt11 cDNA library constructed with 7.5-day-old chicken embryonic brain mRNA [*Journal of Cell Biology*, 106, p873–881 (1988)] was screened using NCAT-1, as described by Huynh et al. [IRL press publisher, *DNA cloning: A practical approach*, 1, p49–78, (1985)].

Approximately $2\times10^5$ recombinants were screened, and five positive clones were obtained. One of these clones, λ1, was used for successive screenings of the λgt11 cDNA library and a λgt10 library from 6.5-day-old chick embryonic brain mRNA [*J. Cell Biol.*, 106, p873–881 (1988)] to obtain overlapping clones. The inventors then screened the λgt10 library using λ1 to obtain longer cDNA clones. The longest clone obtained, λG, was still not full length. Thus, using an upstream PstI fragment of λG, the λgt11 library was rescreened, and clone λ8-2 was obtained. To obtain the full-length cDNA, the inventors further screened the λgt10 library using λ8-2, and the longest clone, λZEN, was isolated.
2-2 Northern Blot Analysis 4 μg of poly(A)$^+$RNA isolated from 10-day-old chicken embryonic brains by the Quick Prep mRNA Purification Kit (Pharmacia) was resolved in a 1% agarose-formaldehyde gel. RNA was transferred to nitrocellulose filters and hybridized at 42° C. in a buffer containing 30% formamide with a probe of $^{32}P$-labeled μ-Zen insert prepared by the T7 Quick Prime Kit (Pharmacia). Northern blot analysis using clone μZEN detected a 4 kb band from embryonic brain RNA.
2-3 Determination of nucleotide sequence The inserts of positive clones were subcloned into the EcoRI site of pBluescript SK(+) (Stratagene) and then sequenced with the 7-deaza Sequenase Version 2.0 kit (US Biochemical). To determine the sequence of longer inserts, the plasmids were linearized and unidirectionally deleted using the Deletion Kit for Kilo-Sequence (Takara Shuzo).

The complete nucleotide sequence of the above cDNA and the deduced amino acid sequence of the cloned molecule are shown by SEQ ID No. 2 in the sequence listing. Then, the deduced amino acid sequence of the molecule is solely shown by SEQ ID No. 1 in the sequence listing.

In the 3123 nucleotides sequence of the inserted DNA in μZEN, the longest open reading frame of 2718 nucleotides begins from an ATG codon at nucleotide 124 and ends with a TAA signal for translation termination at nucleotide 2842. This open reading frame encodes a polypeptide of 906 amino acids with a predicted molecular mass of 100,686 daltons. The predicted amino acid sequence of this molecule showed 81.6% identity to that of α-catenin or CAP102, which was previously reported [*Cell*, 65, p849–857 (1991), and *Proceedings of the National Academy of Sciences of the USA*, 88, p9156–9160 (1991)]. α-Catenin shows similarity to vinculin [*Cell*, 65, p849–857 (1991)], this molecule also showed similarity to chicken vinculin. Namely, amino acid sequences 21–223, 376–584, and 698–848 of neural α-catenin were 25.6%, 28.8%, and 35.8% identical to those of 6–208, 582–796, and 905–1053 of chicken vinculin, respectively. From these result, the inventors determined that the molecule was a novel subtype of α-catenin which exists richly in nervous tissues. This molecule was designated as neural α-catenin.

Example 3

3-1 Construction of expression vectors

The expression vector of neural α-catenin cDNA, pMiw-αN, was constructed as follows. λZEN containing neural α-catenin cDNA was isolated by EcoRI digestion from the pBluescript vector, blunted with T4 polymerase, and then inserted into the expression vector pMiwCAT [*Molecular and Cellular Biology*, 10, p486–491 (1990)].

This was performed by replacing CAT region with λZEN in the vector by digestion with HindIII and HpaI and blunting.

3-2 Expression in the animal cells

Transfection of cNLm-1 [*Development*, 110, p97–104 (1990)] and ELβ1 [*Cell*, 54, p993–1001 (1988)] cells with neural α-catenin cDNA was done with slight modifications of the method of Nose et al. [*Cell*, 54, p993–1001 (1988)]. For selection of transfectants, cells were cotransfected with pSV2hph encoding the hygromycin B phosphotransferase gene [*Gene*, 30, p147–156 (1984), and IRL press publisher, *DNA cloning: a practical approach*, 2, p143–190 (1985)] and incubated with 0.2 mg/ml hygromycin B. For transfection of PC9 cells [*British Journal of Cancer*, 39, p2–23 (1979)], vector pMiw-αN was introduced by electroporation. PC9 cells ($1 \times 10^5$) were mixed with 10 μg of pMiw-αN and 1 μg of vector pGKneo bpA [*Gene*, 30, p147–156 (1984)] in 10 mM HEPES-buffered saline containing 1 mM CaCl$_2$. Electroporation was performed at 820 μF and 200V. Transfected cells were selected using 0.2 mg/ml G418. The stable expression of the antigen in each transfected cell was identified by immunoblotting analysis using NCAT-2 monoclonal antibody.

Moreover, the present inventors identified that the cell-cell adhesive property was obtained in the DNA-transfected cells, and that the antigen was detected between cell-cell contract region by immunofluorescence staining using NCAT-1 or NCAT-2 monoclonal antibody. Cultured cells on culture dishes were fixed with 3.5% parformaldehyde for 30 min on ice. After permeabilization by treatment with −20° C. methanol for 10 min, cells were incubated with 2.5% skim milk in TBS containing 1 mM CaCl$_2$ and successively treated with first antibodies (anti-E-cadherin, anti-N-cadherin, or anti-neural α-catenin), secondary antibodies conjugated with biotin, and fluorescence dye-coupled streptavidin.

Example 4

4-1 Detection of neural α-catenin in animal cells cNLm-1 and ELβ1 cells were transfected with neural α-catenin cDNA obtained in example 3-1 to obtain NL-αN51 and EL-αN28 lines, respectively.

Immunoblots were performed to detect neural α-catenin using NCAT-2, N-cadherin using NCD-2, and E-cadherin using ECCD-2 [*Cell Structure and Function*, 11, p245–252 (1986)]. As a result, the 113 kda and 102 kda protein bands were detected in chick brain extract by NCAT-2 monoclonal antibody, and only the 102 kda band was detected in the transfectants, NL-αN51 and EL-αN28 cells.

N-cadherin, which was recognized by NCD-2 monoclonal antibody, was identified to be present in NL-αN51 and cNLm-1 cells, and E-cadherin, which was recognized by ECCD-2 monoclonal antibody was identified to be expressed in EL-αN28 and ELβ1 cells.

However, no proteins could not be detected to be recognized by NCAT-2 monoclonal antibody in cNLm-1 and ELβ1 cells, demonstrating that the protein produced by the cells transfected with neural α-catenin DNA was recognized by NCAT-1 or NCAT-2 monoclonal antibody. Thus, the isolated cDNA, λZEN, encodes at least one of the NCAT-1 and NCAT-2 antigens. L cells without cadherins could not stably express neural α-catenin proteins even when transfected with neural α-catenin cDNA, as found previously for α-catenin [*Cell*, 65,p849–857 (1991)].

According to the method of example 1-1, N-cadherin-catenin complex was isolated from the extracts of NL-αN51 cells, and similarly, E-cadherin-catenin complex was isolated from the extracts of EL-αN28 cells by using immunoaffinity column chromatography of ECCD-2 monoclonal antibody. These cadherin-catenin complexs were separated electrophoretically and analysed by immnoblotting. The results demonstrated that N-cadherin reactive with NCD-2 monoclonal antibody was associated with neural α-catenin reactive with NCAT-2 monoclonal antibody, and that E-cadherin reactive with ECCD-2 monoclonal antibody was associated with neural α-catenin reactive with NCAT-2 monoclonal antibody. The result of immnoblotting shows that neural α-catenin can coimmunoprecipitate with both E- and N-cadherin. Similar results were obtained for α-catenin. Thus, each catenin can associate with both of these cadherins.

Example 5

5-1 Expression of neural α-catenin in α-catenin-deficient cells

The extract of non-treated and neural α-catenin cDNA-transfected PC9 cells obtained in example 3-2 were separated on electrophoresis and analysed by immunoblotting. Thus, human E-cadherin was detected in PC9 cells by using HECD-1 monoclonal antibody [*Cancer Research*, 49, p2128–2133 (1989)], and β-catenin was also detected in these cells by an anti-armadillo antiserum that is known to cross-react with this catenin of the vertebrate [*Journal of Cell Biology*, 118, p681–691 (1992)]. But α-catenin could not be detected in these cells by MAb1809 monoclonal antibody (a gift from Dr. A. Nagafuchi and Dr. S. Tsukita) and neural α-catenin could not be detected in these cells by NCAT-2.

The PC9 cells transfected with neural α-catenin cDNA expressed E-cadherin, β-catenin and neural α-catenin, which were reactive with HECD-1, anti-armadillo antiserum, and NCAT-2, respectively. But, these transfected cells expressed no α-catenin reactive with MAb1809 monoclonal antibody. These results showed that PC9 cells expressing E-cadherin, β-catenin, and no α-catenin, could newly express neural α-catenin when they were transfected with neural α-catenin cDNA.

E-cadherin- or N-cadherin-catenin complex, isolated from the extracts of the cells transfected with neural α-catenin cDNA by using HECD-1 or NCD-2 monoclonal antibodies immobilized on column, were separated electrophoretically and analysed by immunoblotting. E-cadherin-catenin complex could be isolated only by using immobilized HECD-1 monoclonal antibody, and neural α-catenin reactive with NCAT-2 could be detected only in the complex.

Thus, neural α-catenin expressed in the cells transfected with neural α-catenin cDNA was found to be associated with E-cadherin expressed simultaneously.

5-2 Analysis of the activity of cell-cell adhesion in the cells expressing neural α-catenin PC9 cells, PC9 cells transfected with neural α-catenin cDNA, and their mixture were immunostained by NCAT-2 or NECD-1 monoclonal antibody, and the close microscopical observation of these aggregates and the immunostained regions was performed. PC9 cells formed the cell clusters whose cell-cell adhesions were very slight. E-cadherin was slightly stained and no neural α-catenin was not identified the cell-cell boundaries in such cell clusters. The cells transfected with neural α-catenin cDNA showed the tight cell-cell adhesions, the cell-cell boundaries in such cell clusters always intensely stained both for E-cadherin and neural α-catenin.

These clusters were then isolated. They gradually grew to larger aggregates in which cells firmly attached to each other, although still did not attach to dishes. All cell-cell boundaries in these aggregates intensely stained for both neural α-catenin and E-cadherin. Close microscopical observations of these aggregates revealed that cells are often arranged into the pattern of closed epithelium-like monolayer sheets. Occasionally, these cells displayed cystic spheres each of which comprises a shell of monolayer cell sheet and a fully expanded lumen. When these aggregates were incubated with antibodies to E-cadherin, they were completely dissociated into single cells, indicating that the E-cadherin adhesion system is responsible for the formation of such aggregates. Neural α-catenin-negative cells never formed compact or epithelial aggregates.

Example 6

6-1 Tissue distribution of neural α-catenin

Immunoblot analysis, according to the method in the example 1-2, of neural α-catenin using various tissues (brain, heart, lung, liver, kidney, leg, muscle, and gizzard ) of 10-day-old chicken embryos revealed that it is most abundant in the brain. The present inventor did not detect high levels of neural α-catenin expression in most tissues whose major cadherin is known to be E-cadherin. Interestingly, the expression of neural α-catenin was not always correlated with that of N-cadherin. For example, the heart intensely expressed N-cadherin but no neural α-catenin.

6-2 Immunostaining for neural α-catenin in brain tissues

To identify cell types expressing neural α-catenin in the brain, monolayer cultures of 10-day-old embryonic brain cells were prepared according to the method by K. Hatta et al. [*Developmental Biology*, 120, p215–227 (1987)]. The neural tube, dorsal root ganglia, spinal nerves, and myotome strongly reacted with NCAT-2, and these tissues also stained for N-cadherin. However, the notochord did not express neural α-catenin, although it did express N-cadherin. Immunostaining of these cultures showed that the expression of this molecule is heterogeneous; that is, some cells are positive while others are negative. The present inventors, however, found that both neuronal and glial populations contain neural α-catenin-positive cells. In the positive neurons, axons stained for this catenin, and, in glia, cell-cell boundaries were intensely stained. In these cells, neural α-catenin colocalized with N-cadherin if both molecules were coexpressed.

Effect of the invention:

This invention provides neural α-catenin which plays significant roles in cell-cell adhesion, a gene encoding neural α-catenin, a method of producing neural α-catenin by the method of genetic engineering, a method of controlling the function of cell-cell adhesion by using said gene, and antibodies capable of recognizing neural α-catenin.

What we claim is:

1. Isolated gene encoding chicken neural α-catenin having an amino acid sequence as shown by SEQ ID No. 1.

2. Isolated gene of claim 1, wherein the nucleotide sequence is as shown by SEQ ID No. 2 in the sequence listing.

3. Isolated gene of claim 1 which is obtainable from the vector pMiw-αN.

4. Isolated gene encoding neural α-catenin which is hybridizable with the gene of claim 1 under stringent conditions.

5. A vector which comprises the isolated gene of claim 1, 2, 3 or 4.

6. A method of producing neural α-catenin which comprises cultivating transfectants containing the vector of claim 5, and isolating neural α-catenin from the culture medium in which the transfectants have been cultivated.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
      ( A ) LENGTH: 906 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL:

( i v ) ANTI-SENSE:

( v ) FRAGMENT TYPE:

( v i ) ORIGINAL SOURCE:
            ( A ) ORGANISM:
            ( B ) STRAIN:
            ( C ) INDIVIDUAL ISOLATE:
            ( D ) DEVELOPMENTAL STAGE:
            ( E ) HAPLOTYPE:
            ( F ) TISSUE TYPE:
            ( G ) CELL TYPE:
            ( H ) CELL LINE:
            ( I ) ORGANELLE:

( v i i ) IMMEDIATE SOURCE:
            ( A ) LIBRARY:
            ( B ) CLONE:

( v i i i ) POSITION IN GENOME:
            ( A ) CHROMOSOME/SEGMENT:
            ( B ) MAP POSITION:
            ( C ) UNITS:

( i x ) FEATURE:
            ( A ) NAME/KEY:
            ( B ) LOCATION:
            ( C ) IDENTIFICATION METHOD:
            ( D ) OTHER INFORMATION:

( x ) PUBLICATION INFORMATION:
            ( A ) AUTHORS:
            ( B ) TITLE:
            ( C ) JOURNAL:
            ( D ) VOLUME:
            ( E ) ISSUE:
            ( F ) PAGES:
            ( G ) DATE:
            ( H ) DOCUMENT NUMBER:
            ( I ) FILING DATE:
            ( J ) PUBLICATION DATE:
            ( K ) RELEVANT RESIDUES IN SEQ ID NO:

( x i ) SEQUENCE DESCRIPTION: SEQ ID NO:1:

| Met | Thr | Ser | Ala | Thr | Ser | Pro | Ile | Ile | Leu | Lys | Trp | Asp | Pro | Lys |
|---|---|---|---|---|---|---|---|---|---|---|---|---|---|---|
| 1 | | | | 5 | | | | | 10 | | | | | 15 |
| Ser | Leu | Glu | Ile | Arg | Thr | Leu | Thr | Val | Glu | Arg | Leu | Leu | Glu | Pro |
| | | | | 20 | | | | | 25 | | | | | 30 |
| Leu | Val | Thr | Gln | Val | Thr | Thr | Leu | Val | Asn | Thr | Ser | Asn | Lys | Gly |
| | | | | 35 | | | | | 40 | | | | | 45 |
| Pro | Ser | Gly | Lys | Lys | Lys | Gly | Arg | Ser | Lys | Lys | Ala | His | Val | Leu |
| | | | | 50 | | | | | 55 | | | | | 60 |
| Ala | Ala | Ser | Val | Glu | Gln | Ala | Thr | Gln | Asn | Phe | Leu | Glu | Lys | Gly |
| | | | | 65 | | | | | 70 | | | | | 75 |
| Asp | Gln | Ile | Ala | Lys | Glu | Ser | Gln | Asp | Leu | Lys | Glu | Glu | Leu | Val |
| | | | | 80 | | | | | 85 | | | | | 90 |
| Ala | Ala | Val | Glu | Asp | Val | Arg | Lys | Gln | Gly | Glu | Thr | Met | Arg | Ile |
| | | | | 95 | | | | | 100 | | | | | 105 |
| Ala | Ser | Ser | Glu | Phe | Ala | Asp | Asp | Pro | Cys | Ser | Ser | Val | Lys | Arg |
| | | | | 110 | | | | | 115 | | | | | 120 |
| Gly | Thr | Met | Val | Arg | Ala | Ala | Arg | Ala | Leu | Leu | Ser | Ala | Val | Thr |
| | | | | 125 | | | | | 130 | | | | | 135 |
| Arg | Leu | Leu | Ile | Leu | Ala | Asp | Met | Ala | Asp | Val | Met | Arg | Leu | Leu |
| | | | | 140 | | | | | 145 | | | | | 150 |
| Ser | His | Leu | Lys | Ile | Val | Glu | Glu | Ala | Leu | Glu | Ala | Val | Lys | Asn |
| | | | | 155 | | | | | 160 | | | | | 165 |
| Ala | Thr | Asn | Glu | Gln | Asp | Leu | Ala | Asn | Arg | Phe | Lys | Glu | Phe | Gly |
| | | | | 170 | | | | | 175 | | | | | 180 |

```
Lys Glu Met Val Lys Leu Asn Tyr Val Ala Ala Arg Arg Gln Gln
            185                 190                 195

Glu Leu Lys Asp Pro His Cys Arg Asp Glu Met Ala Ala Ala Arg
            200                 205                 210

Gly Ala Leu Lys Lys Asn Ala Thr Met Leu Tyr Thr Ala Ser Gln
            215                 220                 225

Ala Phe Leu Arg His Pro Asp Val Ala Ala Thr Arg Ala Asn Arg
            230                 235                 240

Asp Tyr Val Phe Lys Gln Val Gln Glu Ala Ile Ala Gly Ile Ser
            245                 250                 255

Asn Ala Ala Gln Ala Thr Ser Pro Thr Asp Glu Asn Lys Gly His
            260                 265                 270

Thr Gly Ile Gly Glu Leu Ala Ala Ala Leu Asn Glu Phe Asp Asn
            275                 280                 285

Lys Ile Ile Leu Asp Pro Met Thr Phe Ser Glu Ala Arg Phe Arg
            290                 295                 300

Pro Ser Leu Glu Glu Arg Leu Glu Ser Ile Ile Ser Gly Ala Ala
            305                 310                 315

Leu Met Ala Asp Ser Ser Cys Thr Arg Asp Asp Arg Arg Lys Arg
            320                 325                 330

Ile Val Ala Glu Cys Lys Arg Ala Val Arg Gln Ala Leu Gln Asp
            335                 340                 345

Leu Leu Ser Glu Tyr Met Asn Asn Thr Gly Arg Lys Glu Lys Gly
            350                 355                 360

Asp Pro Leu Asn Ile Ala Ile Asp Lys Met Thr Lys Lys Thr Arg
            365                 370                 375

Asp Leu Arg Arg Gln Leu Arg Lys Ala Val Met Asp His Ile Ser
            380                 385                 390

Asp Ser Phe Leu Glu Thr Asn Val Pro Leu Leu Val Leu Ile Glu
            395                 400                 405

Ala Ala Lys Ser Gly Asn Glu Lys Glu Val Lys Glu Tyr Ala Gln
            410                 415                 420

Val Phe Arg Glu His Ala Asn Lys Leu Val Glu Val Ala Asn Leu
            425                 430                 435

Ala Cys Ser Ile Ser Asn Asn Glu Glu Gly Val Lys Leu Val Arg
            440                 445                 450

Met Ala Ala Thr Gln Ile Asp Ser Leu Cys Pro Gln Val Ile Asn
            455                 460                 465

Ala Ala Leu Thr Leu Ala Ala Arg Pro Gln Ser Lys Val Ala Gln
            470                 475                 480

Asp Asn Met Asp Val Phe Lys Asp Gln Trp Glu Lys Gln Val Arg
            485                 490                 495

Val Leu Thr Glu Ala Val Asp Asp Ile Thr Ser Val Asp Asp Phe
            500                 505                 510

Leu Ser Val Ser Glu Asn His Ile Leu Glu Asp Val Asn Lys Cys
            515                 520                 525

Val Ile Ala Leu Gln Glu Gly Asp Val Asp Thr Leu Asp Arg Thr
            530                 535                 540

Ala Gly Ala Ile Arg Gly Arg Ala Ala Arg Val Ile His Ile Ile
            545                 550                 555

Asn Ala Glu Met Glu Asn Tyr Glu Thr Gly Val Tyr Thr Glu Lys
            560                 565                 570

Val Leu Glu Ala Thr Lys Leu Leu Ser Glu Thr Val Met Pro Arg
```

|          |     |     |     | 575 |     |     |     |     | 580 |     |     |     |     | 585 |
|----------|-----|-----|-----|-----|-----|-----|-----|-----|-----|-----|-----|-----|-----|-----|
| Phe | Ala | Glu | Gln | Val | Glu | Val | Ala | Ile | Glu | Ala | Leu | Ser | Ala | Asn |
|     |     |     |     | 590 |     |     |     |     | 595 |     |     |     |     | 600 |
| Val | Pro | Gln | Pro | Phe | Glu | Glu | Asn | Glu | Phe | Ile | Asp | Ala | Ser | Arg |
|     |     |     |     | 605 |     |     |     |     | 610 |     |     |     |     | 615 |
| Leu | Val | Tyr | Asp | Gly | Val | Arg | Asp | Ile | Arg | Lys | Ala | Val | Leu | Met |
|     |     |     |     | 620 |     |     |     |     | 625 |     |     |     |     | 630 |
| Ile | Arg | Thr | Pro | Glu | Glu | Leu | Glu | Asp | Asp | Ser | Asp | Phe | Glu | Gln |
|     |     |     |     | 635 |     |     |     |     | 640 |     |     |     |     | 645 |
| Glu | Asp | Tyr | Asp | Val | Arg | Ser | Arg | Thr | Ser | Val | Gln | Thr | Glu | Asp |
|     |     |     |     | 650 |     |     |     |     | 655 |     |     |     |     | 660 |
| Asp | Gln | Leu | Ile | Ala | Gly | Gln | Ser | Ala | Arg | Ala | Ile | Met | Ala | Gln |
|     |     |     |     | 665 |     |     |     |     | 670 |     |     |     |     | 675 |
| Leu | Pro | Gln | Glu | Glu | Lys | Ala | Lys | Ile | Ala | Glu | Gln | Val | Glu | Ile |
|     |     |     |     | 680 |     |     |     |     | 685 |     |     |     |     | 690 |
| Phe | His | Gln | Glu | Lys | Ser | Lys | Leu | Asp | Ala | Glu | Val | Ala | Lys | Trp |
|     |     |     |     | 695 |     |     |     |     | 700 |     |     |     |     | 705 |
| Asp | Asp | Ser | Gly | Asn | Asp | Ile | Ile | Val | Leu | Ala | Lys | Gln | Met | Cys |
|     |     |     |     | 710 |     |     |     |     | 715 |     |     |     |     | 720 |
| Met | Ile | Met | Met | Glu | Met | Thr | Asp | Phe | Thr | Arg | Gly | Lys | Gly | Pro |
|     |     |     |     | 725 |     |     |     |     | 730 |     |     |     |     | 735 |
| Leu | Lys | Asn | Thr | Ser | Asp | Val | Ile | Asn | Ala | Ala | Lys | Lys | Ile | Ala |
|     |     |     |     | 740 |     |     |     |     | 745 |     |     |     |     | 750 |
| Glu | Ala | Gly | Ser | Arg | Met | Asp | Lys | Leu | Ala | Arg | Ala | Val | Ala | Asp |
|     |     |     |     | 755 |     |     |     |     | 760 |     |     |     |     | 765 |
| Gln | Cys | Pro | Asp | Ser | Ala | Cys | Lys | Gln | Asp | Leu | Leu | Ala | Tyr | Leu |
|     |     |     |     | 770 |     |     |     |     | 775 |     |     |     |     | 780 |
| Gln | Arg | Ile | Ala | Leu | Tyr | Cys | His | Gln | Leu | Asn | Ile | Cys | Ser | Lys |
|     |     |     |     | 785 |     |     |     |     | 790 |     |     |     |     | 795 |
| Val | Lys | Ala | Glu | Val | Gln | Asn | Leu | Gly | Gly | Glu | Leu | Ile | Val | Ser |
|     |     |     |     | 800 |     |     |     |     | 805 |     |     |     |     | 810 |
| Gly | Leu | Asp | Ser | Ala | Thr | Ser | Leu | Ile | Gln | Ala | Ala | Lys | Asn | Leu |
|     |     |     |     | 815 |     |     |     |     | 820 |     |     |     |     | 825 |
| Met | Asn | Ala | Val | Val | Leu | Thr | Val | Lys | Ala | Ser | Tyr | Val | Ala | Ser |
|     |     |     |     | 830 |     |     |     |     | 835 |     |     |     |     | 840 |
| Thr | Lys | Tyr | Gln | Lys | Val | Tyr | Gly | Thr | Ala | Ala | Val | Asn | Ser | Pro |
|     |     |     |     | 845 |     |     |     |     | 850 |     |     |     |     | 855 |
| Val | Val | Ser | Trp | Lys | Met | Lys | Ala | Pro | Glu | Lys | Lys | Pro | Leu | Val |
|     |     |     |     | 860 |     |     |     |     | 865 |     |     |     |     | 870 |
| Lys | Arg | Glu | Lys | Pro | Glu | Glu | Tyr | Gln | Thr | Arg | Val | Arg | Arg | Gly |
|     |     |     |     | 875 |     |     |     |     | 880 |     |     |     |     | 885 |
| Ser | Gln | Lys | Lys | His | Ile | Ser | Pro | Val | Gln | Ala | Leu | Ser | Glu | Phe |
|     |     |     |     | 890 |     |     |     |     | 895 |     |     |     |     | 900 |
| Lys | Ala | Met | Asp | Ser | Phe |     |     |     |     |     |     |     |     |     |
|     |     |     |     | 905 |     |     |     |     |     |     |     |     |     |     |

( 2 ) INFORMATION FOR SEQ ID NO:2:

( i ) SEQUENCE CHARACTERISTICS:
        ( A ) LENGTH: 3123 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL:

( i v ) ANTI-SENSE:

( v ) FRAGMENT TYPE:

( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:
    ( A ) LIBRARY:
    ( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY:
    ( B ) LOCATION:
    ( C ) IDENTIFICATION METHOD:
    ( D ) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:2:

```
GGGAGTCGTG CTGCACACCC AGCCCGTAAG TAAACGCCGC TGCTGGAGAG GAGGAGGAGG        60

AGGAGAAGGA GGCGGCGGCG GCGGCGAGAG GTTCTCCCAC CCCCACCCAC CGAGCTGAGG       120

GAGT ATG ACT TCT GCA ACG TCA CCT ATC ATT TTG AAA TGG GAC                163
     Met Thr Ser Ala Thr Ser Pro Ile Ile Leu Lys Trp Asp
     1               5                   10

CCC AAA AGT TTG GAA ATC AGG ACT CTC ACA GTA GAG AGG CTA CTG            208
Pro Lys Ser Leu Glu Ile Arg Thr Leu Thr Val Glu Arg Leu Leu
        15              20                  25

GAG CCA CTC GTT ACT CAG GTA ACA ACA CTC GTT AAC ACA AGC AAC            253
Glu Pro Leu Val Thr Gln Val Thr Thr Leu Val Asn Thr Ser Asn
        30              35                  40

AAG GGA CCA TCT GGC AAG AAG AAA GGG CGC TCC AAG AAG GCC CAT            298
Lys Gly Pro Ser Gly Lys Lys Lys Gly Arg Ser Lys Lys Ala His
        45              50                  55

GTG TTG GCT GCC TCC GTA GAG CAG GCT ACT CAA AAC TTT TTA GAG            343
Val Leu Ala Ala Ser Val Glu Gln Ala Thr Gln Asn Phe Leu Glu
        60              65                  70

AAA GGA GAT CAA ATT GCT AAA GAG AGC CAG GAT CTG AAG GAG GAA            388
Lys Gly Asp Gln Ile Ala Lys Glu Ser Gln Asp Leu Lys Glu Glu
        75              80                  85

CTG GTT GCT GCT GTG GAG GAT GTA CGC AAA CAA GGA GAA ACA ATG            433
Leu Val Ala Ala Val Glu Asp Val Arg Lys Gln Gly Glu Thr Met
        90              95                  100
```

| | | | | | | | | | | | | | | | |
|---|---|---|---|---|---|---|---|---|---|---|---|---|---|---|---|
| AGA | ATT | GCC | TCT | TCA | GAG | TTT | GCA | GAC | GAC | CCA | TGC | TCC | TCA | GTG | 478 |
| Arg | Ile 105 | Ala | Ser | Ser | Glu | Phe 110 | Ala | Asp | Asp | Pro | Cys 115 | Ser | Ser | Val | |
| AAG | CGG | GGC | ACG | ATG | GTG | AGG | GCT | GCT | CGT | GCC | TTG | CTT | TCT | GCT | 523 |
| Lys | Arg 120 | Gly | Thr | Met | Val | Arg 125 | Ala | Ala | Arg | Ala | Leu 130 | Leu | Ser | Ala | |
| GTT | ACC | CGC | TTG | CTC | ATC | CTG | GCT | GAT | ATG | GCG | GAC | GTC | ATG | AGG | 568 |
| Val | Thr 135 | Arg | Leu | Leu | Ile | Leu 140 | Ala | Asp | Met | Ala | Asp 145 | Val | Met | Arg | |
| CTT | CTT | TCA | CAT | CTG | AAA | ATT | GTA | GAG | GAA | GCA | CTA | GAA | GCA | GTG | 613 |
| Leu | Leu 150 | Ser | His | Leu | Lys | Ile 155 | Val | Glu | Glu | Ala | Leu 160 | Glu | Ala | Val | |
| AAA | AAT | GCA | ACA | AAT | GAA | CAA | GAT | TTA | GCA | AAT | CGC | TTC | AAA | GAA | 658 |
| Lys | Asn 165 | Ala | Thr | Asn | Glu | Gln 170 | Asp | Leu | Ala | Asn | Arg 175 | Phe | Lys | Glu | |
| TTT | GGA | AAA | GAG | ATG | GTG | AAA | CTG | AAT | TAT | GTA | GCT | GCA | CGG | CGA | 703 |
| Phe | Gly 180 | Lys | Glu | Met | Val | Lys 185 | Leu | Asn | Tyr | Val | Ala 190 | Ala | Arg | Arg | |
| CAG | CAG | GAG | CTG | AAA | GAT | CCT | CAC | TGC | AGG | GAT | GAA | ATG | GCT | GCA | 748 |
| Gln | Gln 195 | Glu | Leu | Lys | Asp | Pro 200 | His | Cys | Arg | Asp | Glu 205 | Met | Ala | Ala | |
| GCT | CGA | GGT | GCT | CTG | AAG | AAG | AAT | GCC | ACA | ATG | TTG | TAT | ACT | GCA | 793 |
| Ala | Arg 210 | Gly | Ala | Leu | Lys | Lys 215 | Asn | Ala | Thr | Met | Leu 220 | Tyr | Thr | Ala | |
| TCC | CAA | GCA | TTT | CTT | CGT | CAC | CCT | GAT | GTT | GCA | GCT | ACT | AGG | GCC | 838 |
| Ser | Gln 225 | Ala | Phe | Leu | Arg | His 230 | Pro | Asp | Val | Ala | Ala 235 | Thr | Arg | Ala | |
| AAC | AGA | GAC | TAT | GTC | TTC | AAG | CAA | GTT | CAA | GAA | GCA | ATT | GCT | GGT | 883 |
| Asn | Arg 240 | Asp | Tyr | Val | Phe | Lys 245 | Gln | Val | Gln | Glu | Ala 250 | Ile | Ala | Gly | |
| ATT | TCC | AAC | GCT | GCC | CAG | GCC | ACC | TCA | CCC | ACT | GAT | GAA | AAC | AAG | 928 |
| Ile | Ser 255 | Asn | Ala | Ala | Gln | Ala 260 | Thr | Ser | Pro | Thr | Asp 265 | Glu | Asn | Lys | |
| GGG | CAT | ACT | GGC | ATT | GGA | GAG | CTT | GCT | GCT | GCA | CTA | AAT | GAA | TTT | 973 |
| Gly | His 270 | Thr | Gly | Ile | Gly | Glu 275 | Leu | Ala | Ala | Ala | Leu 280 | Asn | Glu | Phe | |
| GAT | AAC | AAA | ATC | ATC | TTA | GAC | CCC | ATG | ACG | TTC | AGC | GAG | GCC | CGC | 1018 |
| Asp | Asn 285 | Lys | Ile | Ile | Leu | Asp 290 | Pro | Met | Thr | Phe | Ser 295 | Glu | Ala | Arg | |
| TTC | AGG | CCC | TCT | CTG | GAG | GAG | AGG | CTG | GAG | AGC | ATT | ATC | AGT | GGG | 1063 |
| Phe | Arg 300 | Pro | Ser | Leu | Glu | Glu 305 | Arg | Leu | Glu | Ser | Ile 310 | Ile | Ser | Gly | |
| GCA | GCG | CTG | ATG | GCA | GAC | TCC | TCG | TGC | ACG | CGG | GAT | GAC | CGC | AGG | 1108 |
| Ala | Ala 315 | Leu | Met | Ala | Asp | Ser 320 | Ser | Cys | Thr | Arg | Asp 325 | Asp | Arg | Arg | |
| AAG | CGC | ATC | GTA | GCT | GAG | TGC | AAA | CGC | GCT | GTG | CGG | CAG | GCA | CTG | 1153 |
| Lys | Arg 330 | Ile | Val | Ala | Glu | Cys 335 | Lys | Arg | Ala | Val | Arg 340 | Gln | Ala | Leu | |
| CAG | GAC | CTG | CTC | AGC | GAG | TAC | ATG | AAC | AAT | ACT | GGA | AGG | AAA | GAG | 1198 |
| Gln | Asp 345 | Leu | Leu | Ser | Glu | Tyr 350 | Met | Asn | Asn | Thr | Gly 355 | Arg | Lys | Glu | |
| AAG | GGG | GAC | CCA | CTC | AAC | ATT | GCT | ATT | GAC | AAG | ATG | ACC | AAG | AAA | 1243 |
| Lys | Gly 360 | Asp | Pro | Leu | Asn | Ile 365 | Ala | Ile | Asp | Lys | Met 370 | Thr | Lys | Lys | |
| ACA | CGA | GAC | CTT | CGA | AGA | CAG | CTC | CGG | AAG | GCA | GTA | ATG | GAT | CAT | 1288 |
| Thr | Arg 375 | Asp | Leu | Arg | Arg | Gln 380 | Leu | Arg | Lys | Ala | Val 385 | Met | Asp | His | |
| ATA | TCA | GAT | TCG | TTC | CTG | GAG | ACC | AAT | GTG | CCA | TTG | CTG | GTT | CTC | 1333 |
| Ile | Ser 390 | Asp | Ser | Phe | Leu | Glu 395 | Thr | Asn | Val | Pro | Leu 400 | Leu | Val | Leu | |

| | | | | | | | | | | | | | | | |
|---|---|---|---|---|---|---|---|---|---|---|---|---|---|---|---|
| ATC | GAG | GCT | GCC | AAA | AGC | GGT | AAT | GAG | AAA | GAA | GTG | AAG | GAG | TAC | 1378 |
| Ile | Glu | Ala | Ala | Lys | Ser | Gly | Asn | Glu | Lys | Glu | Val | Lys | Glu | Tyr | |
| | 405 | | | | 410 | | | | | 415 | | | | | |
| GCG | CAG | GTC | TTC | CGT | GAG | CAT | GCC | AAC | AAG | CTC | GTT | GAG | GTT | GCA | 1423 |
| Ala | Gln | Val | Phe | Arg | Glu | His | Ala | Asn | Lys | Leu | Val | Glu | Val | Ala | |
| | 420 | | | | 425 | | | | | 430 | | | | | |
| AAT | CTG | GCC | TGT | TCC | ATC | TCA | AAT | AAT | GAA | GAA | GGT | GTG | AAG | CTA | 1468 |
| Asn | Leu | Ala | Cys | Ser | Ile | Ser | Asn | Asn | Glu | Glu | Gly | Val | Lys | Leu | |
| | 435 | | | | 440 | | | | | 445 | | | | | |
| GTG | CGT | ATG | GCA | GCA | ACA | CAG | ATT | GAT | AGT | CTG | TGC | CCC | CAG | GTA | 1513 |
| Val | Arg | Met | Ala | Ala | Thr | Gln | Ile | Asp | Ser | Leu | Cys | Pro | Gln | Val | |
| | 450 | | | | 455 | | | | | 460 | | | | | |
| ATA | AAT | GCT | GCG | CTG | ACG | TTG | GCT | GCC | AGA | CCT | CAG | AGC | AAA | GTA | 1558 |
| Ile | Asn | Ala | Ala | Leu | Thr | Leu | Ala | Ala | Arg | Pro | Gln | Ser | Lys | Val | |
| | 465 | | | | 470 | | | | | 475 | | | | | |
| GCA | CAG | GAC | AAC | ATG | GAT | GTC | TTT | AAG | GAT | CAG | TGG | GAG | AAA | CAA | 1603 |
| Ala | Gln | Asp | Asn | Met | Asp | Val | Phe | Lys | Asp | Gln | Trp | Glu | Lys | Gln | |
| | 480 | | | | 485 | | | | | 490 | | | | | |
| GTG | CGA | GTT | CTC | ACT | GAA | GCA | GTT | GAT | GAC | ATC | ACT | TCA | GTG | GAT | 1648 |
| Val | Arg | Val | Leu | Thr | Glu | Ala | Val | Asp | Asp | Ile | Thr | Ser | Val | Asp | |
| | 495 | | | | 500 | | | | | 505 | | | | | |
| GAT | TTC | CTC | TCT | GTT | TCA | GAA | AAT | CAT | ATT | CTG | GAA | GAT | GTG | AAC | 1693 |
| Asp | Phe | Leu | Ser | Val | Ser | Glu | Asn | His | Ile | Leu | Glu | Asp | Val | Asn | |
| | 510 | | | | 515 | | | | | 520 | | | | | |
| AAA | TGT | GTG | ATT | GCT | CTC | CAA | GAG | GGA | GAT | GTC | GAT | ACC | CTG | GAT | 1738 |
| Lys | Cys | Val | Ile | Ala | Leu | Gln | Glu | Gly | Asp | Val | Asp | Thr | Leu | Asp | |
| | 525 | | | | 530 | | | | | 535 | | | | | |
| AGA | ACT | GCT | GGG | GCC | ATC | CGA | GGC | CGT | GCA | GCC | AGA | GTC | ATT | CAC | 1783 |
| Arg | Thr | Ala | Gly | Ala | Ile | Arg | Gly | Arg | Ala | Ala | Arg | Val | Ile | His | |
| | 540 | | | | 545 | | | | | 550 | | | | | |
| ATC | ATT | AAT | GCA | GAG | ATG | GAA | AAC | TAT | GAA | ACT | GGA | GTT | TAT | ACC | 1828 |
| Ile | Ile | Asn | Ala | Glu | Met | Glu | Asn | Tyr | Glu | Thr | Gly | Val | Tyr | Thr | |
| | 555 | | | | 560 | | | | | 565 | | | | | |
| GAG | AAG | GTA | CTG | GAA | GCA | ACC | AAA | CTG | CTC | TCT | GAA | ACA | GTT | ATG | 1873 |
| Glu | Lys | Val | Leu | Glu | Ala | Thr | Lys | Leu | Leu | Ser | Glu | Thr | Val | Met | |
| | 570 | | | | 575 | | | | | 580 | | | | | |
| CCA | CGT | TTT | GCT | GAA | CAA | GTT | GAG | GTT | GCC | ATT | GAA | GCG | TTG | AGT | 1918 |
| Pro | Arg | Phe | Ala | Glu | Gln | Val | Glu | Val | Ala | Ile | Glu | Ala | Leu | Ser | |
| | 585 | | | | 590 | | | | | 595 | | | | | |
| GCG | AAT | GTC | CCA | CAG | CCA | TTT | GAA | GAG | AAT | GAG | TTC | ATA | GAT | GCC | 1963 |
| Ala | Asn | Val | Pro | Gln | Pro | Phe | Glu | Glu | Asn | Glu | Phe | Ile | Asp | Ala | |
| | 600 | | | | 605 | | | | | 610 | | | | | |
| TCC | CGC | TTG | GTT | TAT | GAT | GGA | GTT | CGT | GAC | ATC | AGG | AAA | GCT | GTT | 2008 |
| Ser | Arg | Leu | Val | Tyr | Asp | Gly | Val | Arg | Asp | Ile | Arg | Lys | Ala | Val | |
| | 615 | | | | 620 | | | | | 625 | | | | | |
| CTG | ATG | ATA | AGG | ACC | CCT | GAA | GAG | CTG | GAG | GAT | GAT | TCA | GAC | TTT | 2053 |
| Leu | Met | Ile | Arg | Thr | Pro | Glu | Glu | Leu | Glu | Asp | Asp | Ser | Asp | Phe | |
| | 630 | | | | 635 | | | | | 640 | | | | | |
| GAG | CAG | GAA | GAT | TAT | GAT | GTT | CGC | AGC | CGA | ACA | AGT | GTT | CAG | ACT | 2098 |
| Glu | Gln | Glu | Asp | Tyr | Asp | Val | Arg | Ser | Arg | Thr | Ser | Val | Gln | Thr | |
| | 645 | | | | 650 | | | | | 655 | | | | | |
| GAA | GAT | GAC | CAG | CTT | ATT | GCT | GGC | CAG | AGT | GCA | AGG | GCT | ATC | ATG | 2143 |
| Glu | Asp | Asp | Gln | Leu | Ile | Ala | Gly | Gln | Ser | Ala | Arg | Ala | Ile | Met | |
| | 660 | | | | 665 | | | | | 670 | | | | | |
| GCT | CAG | CTC | CCC | CAG | GAG | GAA | AAG | GCT | AAG | ATT | GCT | GAG | CAG | GTA | 2188 |
| Ala | Gln | Leu | Pro | Gln | Glu | Glu | Lys | Ala | Lys | Ile | Ala | Glu | Gln | Val | |
| | 675 | | | | 680 | | | | | 685 | | | | | |
| GAG | ATA | TTC | CAC | CAA | GAA | AAG | AGC | AAA | CTG | GAT | GCA | GAG | GTA | GCC | 2233 |
| Glu | Ile | Phe | His | Gln | Glu | Lys | Ser | Lys | Leu | Asp | Ala | Glu | Val | Ala | |

|     |     |     |     |     |     |     |     |     |     |     |     |     |     |     |      |
| --- | --- | --- | --- | --- | --- | --- | --- | --- | --- | --- | --- | --- | --- | --- | ---- |
|     |     | 690 |     |     |     |     | 695 |     |     |     |     | 700 |     |     |      |
| AAG | TGG | GAT | GAC | AGC | GGT | AAT | GAC | ATC | ATT | GTG | TTG | GCA | AAA | CAG | 2278 |
| Lys | Trp | Asp | Asp | Ser | Gly | Asn | Asp | Ile | Ile | Val | Leu | Ala | Lys | Gln |      |
|     | 705 |     |     |     |     | 710 |     |     |     |     | 715 |     |     |     |      |
| ATG | TGC | ATG | ATT | ATG | ATG | GAA | ATG | ACA | GAC | TTC | ACT | AGA | GGT | AAA | 2323 |
| Met | Cys | Met | Ile | Met | Met | Glu | Met | Thr | Asp | Phe | Thr | Arg | Gly | Lys |      |
|     | 720 |     |     |     |     | 725 |     |     |     |     | 730 |     |     |     |      |
| GGC | CCA | CTG | AAG | AAT | ACA | TCT | GAT | GTC | ATT | AAT | GCA | GCC | AAG | AAG | 2368 |
| Gly | Pro | Leu | Lys | Asn | Thr | Ser | Asp | Val | Ile | Asn | Ala | Ala | Lys | Lys |      |
|     | 735 |     |     |     |     | 740 |     |     |     |     | 745 |     |     |     |      |
| ATT | GCA | GAG | GCA | GGA | TCA | AGG | ATG | GAC | AAA | CTT | GCA | CGG | GCA | GTA | 2413 |
| Ile | Ala | Glu | Ala | Gly | Ser | Arg | Met | Asp | Lys | Leu | Ala | Arg | Ala | Val |      |
|     | 750 |     |     |     |     | 755 |     |     |     |     | 760 |     |     |     |      |
| GCT | GAT | CAG | TGC | CCT | GAC | TCA | GCC | TGC | AAA | CAG | GAC | CTG | CTA | GCC | 2458 |
| Ala | Asp | Gln | Cys | Pro | Asp | Ser | Ala | Cys | Lys | Gln | Asp | Leu | Leu | Ala |      |
|     | 765 |     |     |     |     | 770 |     |     |     |     | 775 |     |     |     |      |
| TAC | CTA | CAG | CGC | ATT | GCC | CTC | TAC | TGC | CAC | CAG | CTC | AAC | ATC | TGC | 2503 |
| Tyr | Leu | Gln | Arg | Ile | Ala | Leu | Tyr | Cys | His | Gln | Leu | Asn | Ile | Cys |      |
|     | 780 |     |     |     |     | 785 |     |     |     |     | 790 |     |     |     |      |
| AGC | AAA | GTC | AAG | GCA | GAA | GTT | CAG | AAC | CTG | GGA | GGA | GAA | CTT | ATT | 2548 |
| Ser | Lys | Val | Lys | Ala | Glu | Val | Gln | Asn | Leu | Gly | Gly | Glu | Leu | Ile |      |
|     | 795 |     |     |     |     | 800 |     |     |     |     | 805 |     |     |     |      |
| GTA | TCA | GGG | CTG | GAC | AGT | GCC | ACT | TCA | CTC | ATC | CAG | GCA | GCT | AAA | 2593 |
| Val | Ser | Gly | Leu | Asp | Ser | Ala | Thr | Ser | Leu | Ile | Gln | Ala | Ala | Lys |      |
|     | 810 |     |     |     |     | 815 |     |     |     |     | 820 |     |     |     |      |
| AAT | CTG | ATG | AAC | GCT | GTG | GTC | CTT | ACA | GTG | AAG | GCA | TCA | TAT | GTA | 2638 |
| Asn | Leu | Met | Asn | Ala | Val | Val | Leu | Thr | Val | Lys | Ala | Ser | Tyr | Val |      |
|     | 825 |     |     |     |     | 830 |     |     |     |     | 835 |     |     |     |      |
| GCT | TCT | ACT | AAG | TAT | CAG | AAG | GTC | TAT | GGT | ACT | GCT | GCA | GTG | AAC | 2683 |
| Ala | Ser | Thr | Lys | Tyr | Gln | Lys | Val | Tyr | Gly | Thr | Ala | Ala | Val | Asn |      |
|     | 840 |     |     |     |     | 845 |     |     |     |     | 850 |     |     |     |      |
| TCC | CCA | GTT | GTA | TCT | TGG | AAG | ATG | AAG | GCA | CCT | GAG | AAG | AAA | CCT | 2728 |
| Ser | Pro | Val | Val | Ser | Trp | Lys | Met | Lys | Ala | Pro | Glu | Lys | Lys | Pro |      |
|     | 855 |     |     |     |     | 860 |     |     |     |     | 865 |     |     |     |      |
| CTA | GTA | AAG | AGA | GAA | AAA | CCA | GAA | GAA | TAT | CAG | ACA | AGA | GTG | AGA | 2773 |
| Leu | Val | Lys | Arg | Glu | Lys | Pro | Glu | Glu | Tyr | Gln | Thr | Arg | Val | Arg |      |
|     | 870 |     |     |     |     | 875 |     |     |     |     | 880 |     |     |     |      |
| AGA | GGG | TCC | CAG | AAG | AAA | CAT | ATT | TCC | CCT | GTA | CAG | GCC | TTA | AGT | 2818 |
| Arg | Gly | Ser | Gln | Lys | Lys | His | Ile | Ser | Pro | Val | Gln | Ala | Leu | Ser |      |
|     | 885 |     |     |     |     | 890 |     |     |     |     | 895 |     |     |     |      |
| GAA | TTT | AAA | GCT | ATG | GAT | TCA | TTC | TAAAACACTA | AGCTTTACCA | GCAGGGTTTT |     |     |     |     | 2872 |
| Glu | Phe | Lys | Ala | Met | Asp | Ser | Phe |     |     |     |     |     |     |     |      |
|     | 900 |     |     |     |     | 905 |     |     |     |     |     |     |     |     |      |
| ATATTCTTTT | TGTATGCATA | CCTGCCGACT | TGTATGCGTC | TGGCATGGGG | TGGGGGGGAA |     |     |     |     |     |     |     |     |     | 2932 |
| GCAGTGTCAA | TTTGCATGTG | ACCTGAAGCT | CTATTGAAGT | AACTACTTTC | TGCAATGCCA |     |     |     |     |     |     |     |     |     | 2992 |
| AAATTTAAGG | GCGTTCTCTT | CCAATGTTCA | GTGGACTTGG | TCCAAGCTTA | CTTTTTAAAC |     |     |     |     |     |     |     |     |     | 3052 |
| TAAACTATTG | CATTAAATTG | GCCAAAGAAT | TTGCATCACA | GGAGTATTTG | CTTGGGTTAA |     |     |     |     |     |     |     |     |     | 3112 |
| ATAATGAATT | C |     |     |     |     |     |     |     |     |     |     |     |     |     | 3123 |